United States Patent
Johannison

(10) Patent No.: US 8,382,731 B2
(45) Date of Patent: Feb. 26, 2013

(54) DEVICE FOR TREATMENT OF WOUND USING REDUCED PRESSURE

(75) Inventor: Ulf Johannison, Landvetter (SE)

(73) Assignee: Molnlycke Health Care AB, Gothenburg (SE)

(*) Notice: Subject to any disclaimer, the term of this patent is extended or adjusted under 35 U.S.C. 154(b) by 185 days.

(21) Appl. No.: 12/936,756

(22) PCT Filed: Apr. 7, 2009

(86) PCT No.: PCT/SE2009/050365
§ 371 (c)(1),
(2), (4) Date: Oct. 7, 2010

(87) PCT Pub. No.: WO2009/126103
PCT Pub. Date: Oct. 15, 2009

(65) Prior Publication Data
US 2011/0028920 A1   Feb. 3, 2011

(30) Foreign Application Priority Data
Apr. 9, 2008  (SE) ...................................... 0800802

(51) Int. Cl.
*A61M 1/00* (2006.01)
*A61M 31/00* (2006.01)
*A61F 13/00* (2006.01)

(52) U.S. Cl. ..................... 604/319; 604/93.01; 604/131; 604/133; 604/304; 604/305; 604/313; 604/317; 604/318; 604/321; 604/322; 604/355; 604/358; 604/378; 604/403; 600/573; 600/578; 600/580

(58) Field of Classification Search ................... 600/573, 600/578, 580; 604/93.1, 131, 133, 304–30, 604/313, 317–319, 321–322, 355, 378, 403
See application file for complete search history.

(56) References Cited

U.S. PATENT DOCUMENTS
(Continued)

FOREIGN PATENT DOCUMENTS

| SE | 0701564-4 | 12/2008 |
|---|---|---|
| WO | WO 2006/025848 | 3/2006 |

(Continued)

OTHER PUBLICATIONS

Chariker, et al. "Effective management of incisional and cutaneous fistulae with closed suction wound drainage." Journal of Contemp. Surg., Jun. 1989, vol. 34, pp. 59-63.

(Continued)

*Primary Examiner* — Jackie Ho
*Assistant Examiner* — Joshua Lee
(74) *Attorney, Agent, or Firm* — Ballard Spahr LLP

(57) ABSTRACT

Provided is a device for treatment of wounds using reduced pressure, which includes a pump, a gas barrier cover, a first compressible material which expands after compression, and a second material capable of absorbing wound fluids several times its own weight. The first and second materials are arranged inside the cover and form a reservoir connected to the pump. The device also includes an inlet for connecting the reservoir with a wound, a wound pad to be arranged in the wound cavity, and a sealing covering the wound and the wound pad. A third material with high liquid spreading capability is arranged around at least a major part of the first material, and the second material is in the form of at least one layer arranged outside the third material and separated from the first material by the third material.

15 Claims, 5 Drawing Sheets

U.S. PATENT DOCUMENTS

| | | | | |
|---|---|---|---|---|
| 3,572,340 | A * | 3/1971 | Lloyd et al. | 604/133 |
| 3,742,952 | A | 7/1973 | Magers | 128/278 |
| 3,871,377 | A | 3/1975 | Treace | 604/133 |
| 4,382,441 | A | 5/1983 | Svedman | 604/291 |
| 4,525,166 | A | 6/1985 | Leclerc | 604/133 |
| 4,537,590 | A | 8/1985 | Pieniak | 604/379 |
| 4,969,880 | A | 11/1990 | Zamierowski | 604/305 |
| 5,385,494 | A | 1/1995 | Wilhelmi | 441/74 |
| 5,636,643 | A | 6/1997 | Argenta | 128/898 |
| 5,645,081 | A | 7/1997 | Argenta | 128/898 |
| 6,855,135 | B2 | 2/2005 | Lockwood | 604/313 |
| 2005/0182347 | A1 * | 8/2005 | Bishop et al. | 602/43 |
| 2007/0219532 | A1 * | 9/2007 | Karpowicz et al. | 604/540 |
| 2010/0324510 | A1 * | 12/2010 | Andresen et al. | 604/319 |

FOREIGN PATENT DOCUMENTS

| | | |
|---|---|---|
| WO | WO 2007/087808 | 8/2007 |
| WO | WO 2008/039223 | 4/2008 |

OTHER PUBLICATIONS

Davydov, et al. "The Bacteriological and Cytological Assessment of Vacuum Therapy of Purulent Wounds." Vestnik Khirurgii, Oct. 1988, pp. 48-52 (published in English in the Kremlin Papers, Perspectives in Wound Care).

Davydov, et al. "Vacuum Therapy in the Treatment of Purulent Lactation Mastitis." Vestnik Khirurgii, Sep. 1986, pp. 66-70 (published in English in The Kremlin Papers, Perspectives in Wound Care).

Davydov, et al. "Concepts for Clinical Biological Management of the Wound Process in the Treatment of Purulent Wounds using Vacuum Therapy." Vestnik Khirurgii, Feb. 1991, pp. 132-135 (published in English in The Kremlin Papers, Perspectives in Wound Care).

Kostiuchenok, et al. "The Vacuum Effect in the Surgical Treatment of Purulent Wounds." Vestnik Khirurgii, Sep. 1986, pp. 18-21 (published in English in The Kremlin Papers, Perspectives in Wound Care).

Usupov, et al. "Active Wound Drainage." Vestnik Khirurgii, 1987, pp. 42-45 (published in English in the Kremlin Papers, Perspectives in Wound Care).

International Search Report and Written Opinion issued Jul. 3, 2009, for International Patent Application No. PCT/SE2009/050365, which was filed on Apr. 7, 2009 (Inventor—Johannison; Applicant—Mölnlycke Health Care AB; pp. 1-9).

International Preliminary Report on Patentability issued Oct. 10, 2010, for International Patent Application No. PCT/SE2009/050365, which was filed on Apr. 7, 2009 (Inventor—Johannison; Applicant—Mölnlycke Health Care AB; pp. 1-5).

* cited by examiner

US 8,382,731 B2

DEVICE FOR TREATMENT OF WOUND USING REDUCED PRESSURE

CROSS REFERENCE TO RELATED APPLICATIONS

The present application is a National Phase Application of International Application No. PCT/SE2009/050365, filed Apr. 7, 2009, which claims priority to Swedish Patent Application No. 0800802-1, filed Apr. 9, 2008, which applications are incorporated herein fully by this reference.

TECHNICAL FIELD

The present invention concerns a device for treatment of wounds using reduced pressure, said device comprising
a pump capable of providing a reduced pressure,
a gas barrier cover,
a first compressible material which is adapted to elastically expand after compression and which contains voids,
a second material that is capable of absorbing wound fluids in an amount several times its own weight and retain it,
said first and second material are arranged inside the cover and form a reservoir connected to said pump,
said device further comprising
an inlet for connecting the reservoir with a wound so as to allow the pump to expose the wound to the reduced pressure,
a wound pad to be arranged in the wound cavity and
a sealing covering the wound and said wound pad.

BACKGROUND ART

Several methods are earlier known for treatment of difficult wounds, such as infected wounds, diabetes wound, pressure sore or deep wounds.

Drainage of for instance operation wounds or other liquid discharging wounds with the aid of negative pressure is a standard treatment that has been used for decades. An example of a manual suction pump for said use is described in U.S. Pat. No. 3,742,952.

In said publication is described a pump in form of an elastically compressible body of an open-cell foam, preferably a polyurethane foam. Said body also serves as a canister for exudate drained from the wound. It is stated that the pump has a capacity to hold a negative pressure of 15-80 mmHg more than 48 hours. A drainage tube is arranged with a perforated end part in the wound cavity and via tube connected to the pump.

A similar device is described in U.S. Pat. No. 4,525,166. In the description of said publication is specifically stated that the negative pressure in addition to drain wound fluids from the wound also presses the edges of the wound together, thereby stimulating rapid tissue granulation and healing of the wound. The two mentioned publication thus teach that vacuum treatment of wounds stimulates the healing of the wounds.

The terms vacuum treatment, treatment at a reduced pressure and treatment with negative pressure are alternatively used in the literature. When using any of this terms in the present description the terms always concern treatment at pressure below normal atmospheric pressure.

Treatment of deep wounds have earlier also been performed by adding an irrigation liquid to the wound and then draining the injected liquid and pus and bacteria present in the wound before the irrigation. Examples of such devices are described in U.S. Pat. Nos. 5,385,494 and 4,382,441.

Extensive investigations of the effect of continuous and intermittent treatment of wounds under negative pressure, i.e. pressure below atmospheric pressure, were performed in the 1980's at Russian institutes. One was able to establish that difficult and normally slow-healing wounds healed considerably faster with the aid of vacuum treatment compared with conventional treatment.

One was inter alia also able to show that treatment at a reduced pressure provides a significant antibacterial effect. Said Russian investigations are described in several articles in the Russian medical journal Vestnik Khirurgii. The relevant articles from said journal are:
1) Kostiuchenok et al, September 1986, pages 18-21.
2) Davydov et al, September 1986, pages 66-70.
3) Usupov et al, April 1987, pages 42-45.
4) Davydov et al, Oktober 1988, pages 48-52.
5) Davydov et al, Februari 1991, pages 132-135.

In an article by Chariker et al in the journal Contemporary Surgery, No. 34, June 1989 is stated that vacuum treatment stimulate tissue granulation and contraction of wounds, which with conventional treatment are very difficult to heal.

Vacuum treatment of wounds is also described in U.S. Pat. No. 4,969,880, U.S. Pat. Nos. 5,645,081, 5,636,643, 6,855,135 B2 and WO 2006/025848 A2.

Hitherto known devices for vacuum treatment of wounds are not satisfactory in every respect.

There is a need for a device which works satisfactory several hours also when the pump is disconnected. It may be necessary to disconnect the pump for instance when the patient is performing an activity or when the patient is travelling. It is also an advantage if the device works and holds a sufficient reduced pressure when there is a malfunction of the pump.

SUMMARY OF THE INVENTION

By means of the present invention an improved device of the type mentioned in the introduction has been achieved. The device in accordance with the invention is characterized in that a third material is arranged around at least a major part of the first material, said third material having high liquid spreading capability, and that said second material is in the form of at least one layer arranged outside the third material and thereby separated from the first material by said third material. With this arrangement the third material will spread absorbed liquid all over the second material and its high absorbent capacity will be fully utilized before the function of the compressible first material is disturbed by absorbed liquid.

According to a preferred embodiment the invention is characterized in that the inlet for wound fluids is arranged to run into the reservoir in connection to the third material.

According to an embodiment the invention is further characterized in that the first material has two opposite major outer surfaces, that said third material is arranged to enclose said major outer surfaces, and that layers of said second material are arranged outside said third materials on both of said two opposite major outer surfaces of the first material.

According to an embodiment the invention is further characterized in that a one-way valve is arranged at the inlet inside the cover and allows gas and liquid to flow in the direction from the wound to the reservoir. With this construction the risk is eliminated that any absorbed wound fluid in the reservoir flows back to the wound.

According to a preferred embodiment the invention is characterized in that said first material is an open-cell foam.

According to an embodiment the invention is characterized in that a major part of said first material is enclosed in a breathable and liquid-tight layer, and that said layer is arranged between the first and the third material. With this arrangement the function of the reservoir is independent of its position on the user's body.

According to an embodiment including said one-way valve the invention is characterized in that said one-way valve is arranged in the end of a tube which in use of the device is connected with a wound, that said one-way valve is arranged to open for allowing gas and liquid from the wound to pass into the reservoir when said pump provides a reduced pressure and that said one-way valve is closed when the pressure in the reservoir is higher than at the wound.

According to an embodiment the invention is further characterized in that said one-way valve comprises a thin, flexible PUR-film, which is arranged to form an open passage when said pump provides a reduced pressure and that said film is arranged to close said passage when the pressure in the reservoir is higher than at the wound, and that said one-way valve formed by the film is protected by a shield which is arranged to form a space within which said film is protected from other forces than caused by the pressure difference between the reservoir and the wound.

According to a modified embodiment the invention is characterized in that said one-way valve has the form of a bag with two main sides and closed around its periphery and sealed around said tube end for forming a bag inlet from the tube to the bag, that said one-way valve has a bag opening on at least one of said sides, that said one-way valve is open with the two main sides at a distance from each other for allowing gas and liquid from the wound to pass into the bag via said bag inlet and out through said bag opening when the pressure around the bag is lower than at the wound, that said one-way valve is closed with said main sides pressed against each other around said bag opening when the pressure around the bag is higher than at the wound, and that said shield defines a space within which the bag can freely expand effected only by the pressure difference between the wound and the reservoir. According to a preferred embodiment the invention is further characterized in that said bag opening is arranged to lead directly to the third material.

According to a further embodiment the invention is characterized in that that said one-way valve is formed by a mainly rectangular thin film applied around said tube end and forming a tubular passage which extends partly over an end part at said tube end and extends further outside said tube end for forming a flexible outer valve part, where the film forming the passage is arranged to be pressed together for closing the passage when the pressure in the reservoir exceeds the pressure in the wound and is arranged to open the passage when a reduced pressure is applied in the reservoir, and that the shield is in form of a protecting tube applied at least over the length of said tubular passage, which protecting tube has an inner diameter which is larger than the outer diameter of said tubular passage.

According to an embodiment the invention is characterized in that said first material is arranged to serve as said suction unit and is capable of providing a reduced pressure upon manual compression, and that a second one-way valve is arranged in said cover for allowing gas to flow out from said suction unit during compression.

According to an embodiment the invention is characterized in that said first material is an open-cell foam, that said first material has at least one hinge along which the foam can be bended and in that the second and third material and the cover are arranged to allow said bending.

According to a modified embodiment the invention is further characterized in that said hinge are arranged to mechanically divide the reservoir in two parts and that the reservoir is foldable along said hinge for facilitate manual compression of the compressible first material.

According to a further embodiment the invention is characterized in that said pump is electrical with a capacity of providing a reduced pressure of at least 10 kPa. With an electrical pump it is possible to maintain the pressure at a certain reduced pressure despite leakage from the device.

BRIEF DESCRIPTION OF THE DRAWINGS

The invention will be described in greater detail below with reference to illustrative embodiments which are shown in the accompanying drawings, in which.

DETAILED DESCRIPTION

Figure 1:
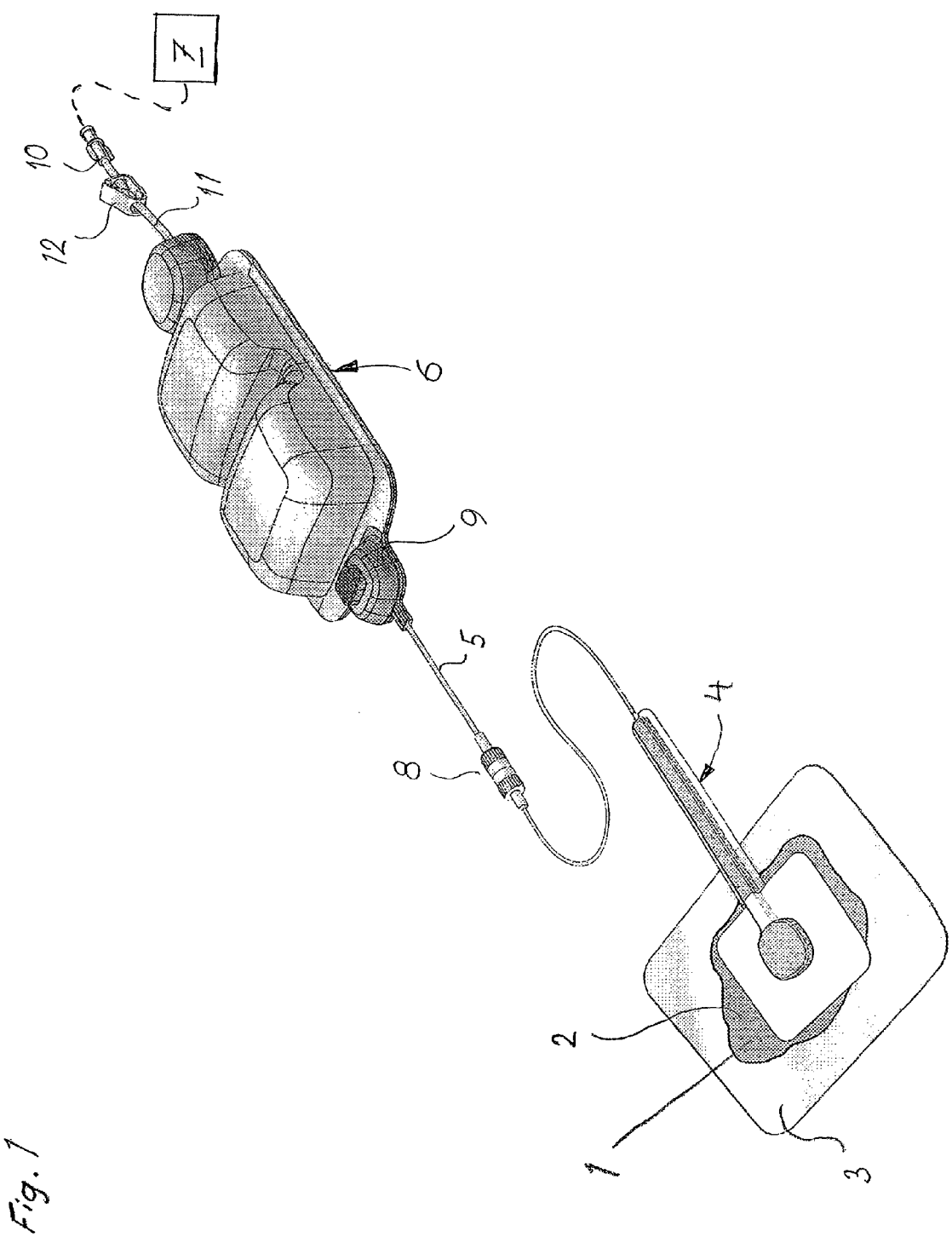
FIG. 1 is a schematic view in perspective of a first embodiment of a device in accordance with the invention during use.

FIG. 1 shows the device in accordance with the invention during use. A wound 1 is schematically illustrated. Within the wound cavity is arranged a wound pad 2, for instance of an open-cell foam. A plastic film 3 serves as a sealing and covers the wound and the wound pad. The plastic film is adhered to the skin of the patient around the wound. A small aperture is arranged in said film over the wound and an adaptor 4 is arranged to connect the wound and the wound pad with an inlet tube 5 to a reservoir 6. The reservoir is connected to a suction pump, which is just schematically indicated at 7. The pump can be an electrical pump which is capable of providing a reduced pressure in the reservoir and wound of about 10–25 kPa.

The construction and function of the adaptor 4 and the sealing film 3 are described in detail in our co-pending Swedish patent application No. 0701546-4. Instead of describing said parts in detail we refer to said application, which contents are incorporated in the description of the present invention. The adaptor 4 is connected with the inlet tube 5 with a luer-lock connection 8.

The device in accordance with the present invention is intended to expose the wound to a reduced pressure in order to stimulate the healing of the wound. The device in accordance with the invention is provided with a leakage indicator 9, which is arranged to indicate when the pressure within the reservoir exceeds a predetermined pressure. In FIG. 1 is shown the female part 10 of a luer-lock connection on an outlet tube 11 from the reservoir. The outlet tube 11 which can be connected to a suction pump 7 and which is manufactured of a flexible plastic material, such as PVC, is provided with a lock clip 12. The lock clip is open when the outlet tube is connected with a suction pump and can be closed by the user or caretaker when the suction pump is disconnected from the device.

The reservoir 6 will be described with reference to FIG. 2. The reservoir includes a first compressible material 20 which is adapted to elastically expand after compression. The material 20 contains interconnected voids, With the expression "interconnected voids" is meant that air can pass all through the material. The purpose with this first material is to create a volume that can hold a reduced pressure for several hours after a suction source is disconnected. A suitable material is an open-cell foam, such as a high density polyurethane foam based on polyether polyol sold under the trade name Eurocel 130, which is extremely elastic and has a density of 110-130 kg/m$^3$ measured according to ISO 845. In the embodiment according to FIG. 2 the first material consists of a bottom piece 201 and two separated top pieces 202 and 203. The reservoir 6 also includes a second material, which is capable of absorbing wound fluids in an amount several times its own weight and retain it also under mechanical pressure. A suitable material is a super absorbent material under the trade name Pilotbond DT 360. This material is supplied in form of a fibrous web and is marked on the drawing with the reference 21. In the embodiment in accordance with FIG. 2 several layers of said superabsorbent web are applied on the opposite main sides of the first material 20.

The reservoir is enclosed in a cover, which comprises a bottom plate 22 of a relatively stiff material and a plastic film 23 joined to the bottom plate. An example of a suitable plastic film is a polyurethane film of a thickness of 150 µm. The plastic film 23 is arranged with extra material with regards to what is needed for an empty reservoir in order to allow the superabsorbent to swell when liquid is absorbed. As shown in FIG. 2 the plastic film 23 and the superabsorbent web are pressed down in the central part between the two top pieces 202,203 of the first material. With such a construction the reservoir gets a central hinge 204 which facilitates the fastening of the reservoir on a rounded body part of a user. The bottom plate 22 is in the shown embodiment arranged to serve as chassis for other parts of the device. An example of material for the bottom plate is polyurethane rubber. The choice of material in the bottom plate is however not critical. In the shown embodiment the leakage indicator 9 is arranged on the bottom plate. The inlet tube 5 extends in a channel in the bottom plate under the leakage indicator into the reservoir and ends with a one-way valve 24, which is arranged to allow gas and liquid to flow in the direction from the wound to the reservoir.

The first material 20, which in the shown embodiment is an open-cell PUR-foam, is enclosed in a breathable and liquid-tight layer 25. This layer forms a pouch around the first material, which pouch is open only at the end of the reservoir where the outlet tube 11 enters the reservoir. The outlet tube 11 enters the reservoir via a pocket 26 and is inserted inside the pouch and extends inside the pouch with its free end 110 close to the bottom 240 of said pouch. A purpose with the arrangement of the outlet tube inside the breathable and liquid-tight pouch is to hinder that liquid from the wound which enters the reservoir via said one-way valve 24 is sucked out through the outlet tube.

A third material 27, which have a high liquid spreading capability and which in the shown embodiment comprises two parts, are arranged to spread liquid absorbed by the reservoir over the major part of the reservoir. One of said parts encircles the top piece 202 and the just opposite part of the bottom piece 201 of the first material and the other encircles the top piece 203 and the just opposite part of the bottom piece 201. The liquid spreading third material 27 is as shown in FIG. 2 arranged outside the pouch 25.

Said second material 21 of a superabsorbent material is arranged in several layers on both major sides of the first material. The second material is arranged outside the third material and the pouch 25 and is thereby separated from the first material by said liquid spreading material and also by the breathable but liquid-tight pouch 25. The superabsorbent layers are just in front of the one-way valve 24 provided with through-holes 210. Liquid from the wound which is sucked into the reservoir through the one-way valve 24 will pass through said holes 210 and reach the liquid spreading material which effectively will spread the liquid all over the reservoir before the liquid is taken up by the superabsorbent material. This material is capable of absorbing wound fluids in an amount several times its own weight but has poor liquid spreading. The use of the spreading material 27 is therefore critical for the function. The webs of superabsorbent material, the second material 21, swell as they absorb liquid. As the plastic film 23 is arranged with extra material with regards to what is needed for an empty reservoir the superabsorbent can swell freely when liquid is absorbed until the available volume inside the cover is fully used. The compressible first material will absorb liquid first after the superabsorbent material is saturated with liquid. The free end 110 of the outlet tube is close to the bottom 250 of the liquid-tight pouch 25. Liquid can only enter the pouch through the opening 251. It is therefore highly unlikely that any liquid will enter the outlet tube through the free end 110. For safety a piece 31 of superabsorbent is applied within the outlet tube 11. A piece of the superabsorbent web as described above can be used. An elongated piece of said web which is twined and then inserted in the outlet tube forms an effective barrier for liquid. The superabsorbent will swell and hinder liquid to pass to the pump.

When a device in accordance with the invention is used on a wound of a patient the pump will create a reduced pressure, i.e. a pressure below atmospheric pressure, within the reservoir and the wound. The first compressible material will be compressed due to the reduced pressure.

If one during wound treatment with reduced pressure wants to disconnect the pump this could be done without negatively effecting the treatment. The tube clip 12 is closed before disconnecting the pump. The compressed first material, the open-cell foam, will retain a reduced pressure within the reservoir and the wound when the pump is disconnected. The system will leak but this is compensated through the elastic expansion of the compressed material. The reservoir as described can for example be dimensioned so that the reduced pressure is maintained at an acceptable level for at least 10 hours. An acceptable level is that the negative pressure is not less than 60 mmHg. A suitable negative pressure during vacuum treatment is about 120-130 mmHg below atmospheric pressure. If the system is dimensioned to work satisfactory for 10 hours the negative pressure should not decrease below 60 mmHg during this period.

The pocket 26 is arranged on the bottom plate 22 and is provided with an opening 260 through which the outlet tube and tube clip can be inserted into the pocket.

One essential problem with vacuum treatment of wound is as mentioned above that it is extremely difficult to maintain the intended reduced pressure in the wound due to air leakage.

A leakage indicator 9 is arranged to indicate when the pressure within the reservoir exceeds a predetermined pressure. The leakage indicator is fastened on the bottom plate 22. Channels 30 connect the interior of the reservoir with a space within the indicator.

Figure 3:
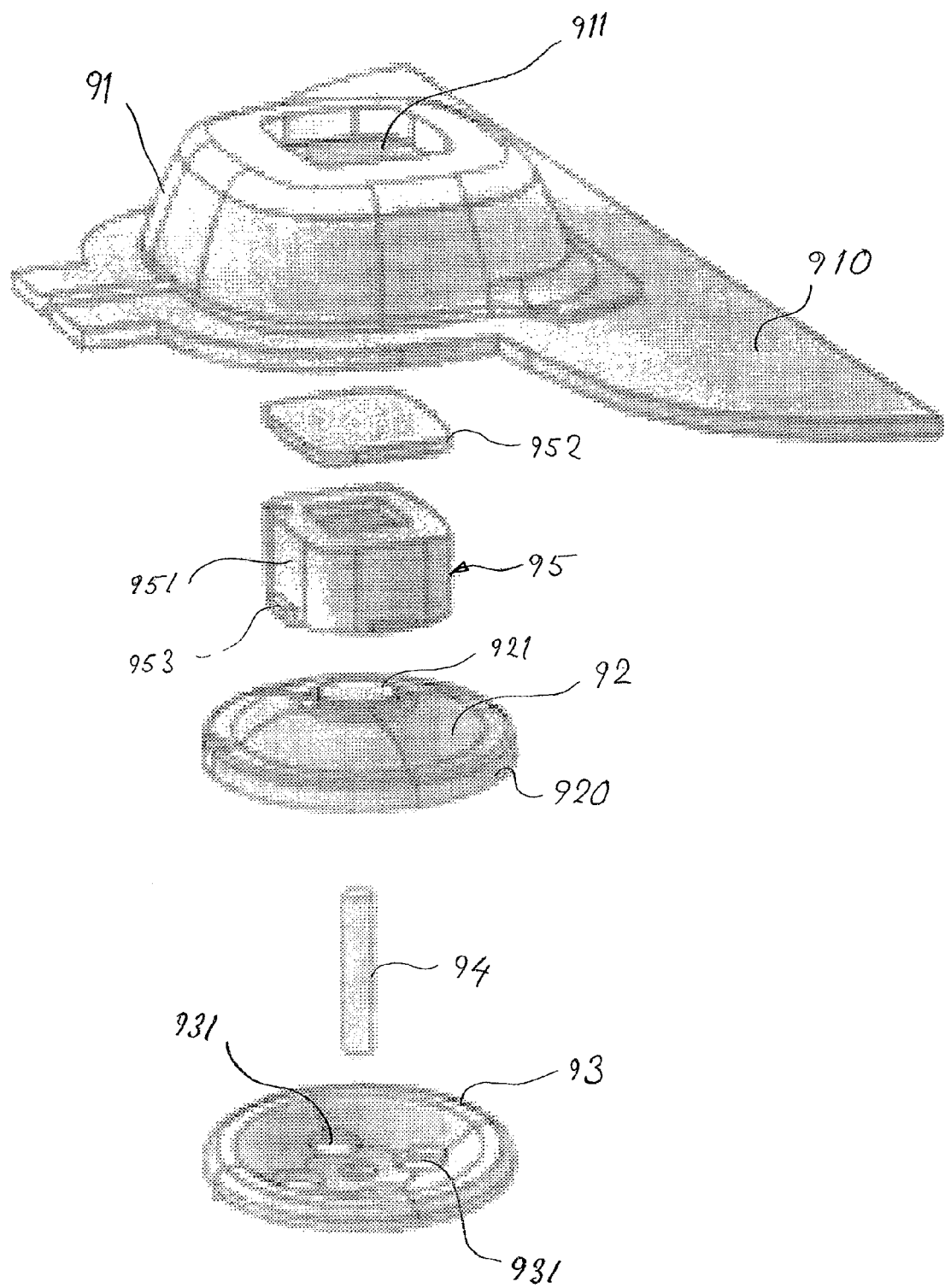
FIG. 3 is an exploded view of a detail of the device in accordance with FIGS. 1 and 2.

The construction and function of an embodiment of the leakage indicator will be described with reference to the exploded view in FIG. 3.

Figure 2:
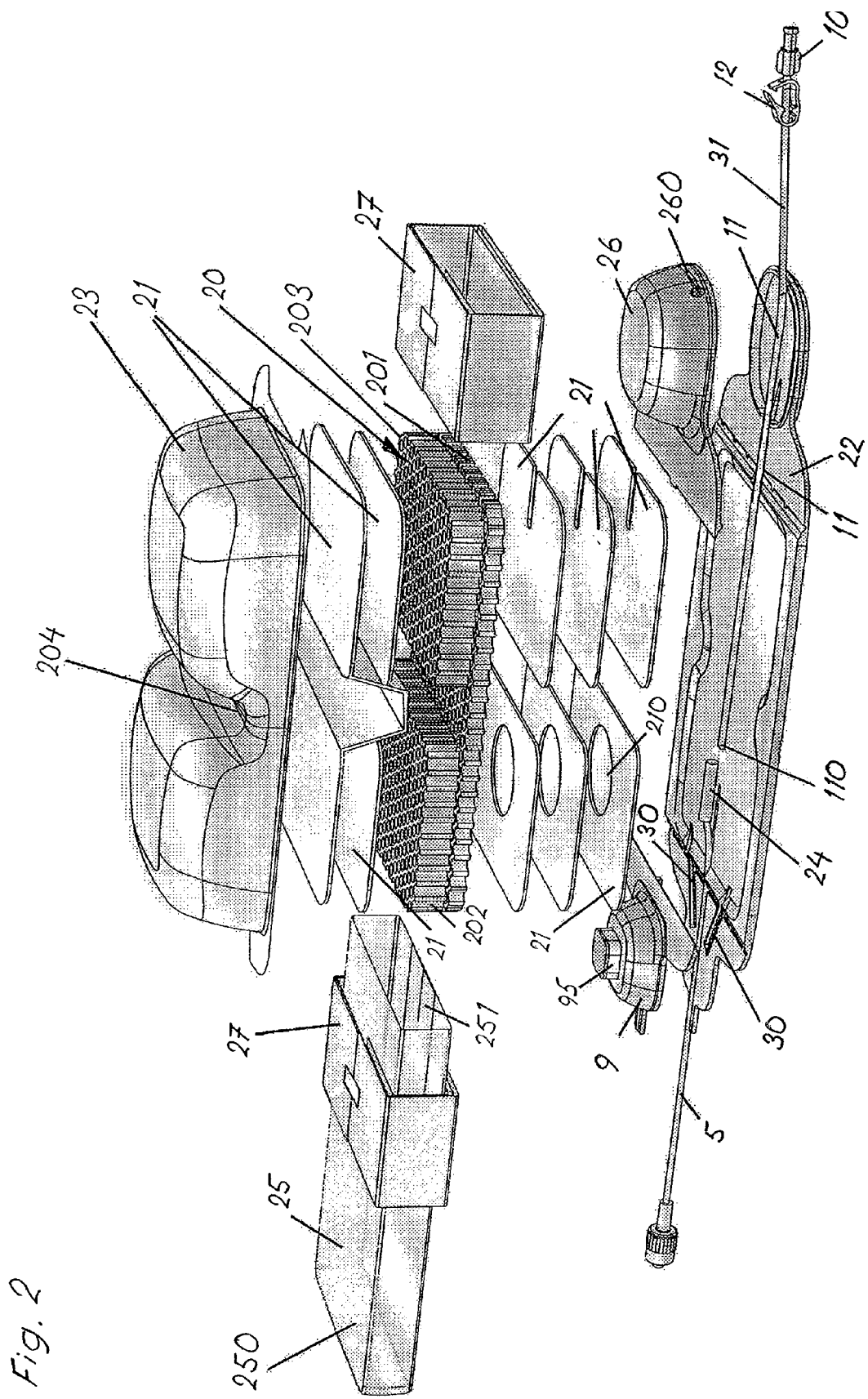
FIG. 2 is an exploded drawing of parts of the device in accordance with FIG. 1.

The leakage indicator 9 comprises a housing 91 with a base plate 910, which as shown in FIG. 2 is fastened on the bottom plate 22. The channels 30 in the bottom plate connect the interior of the reservoir with the interior of the housing 91.

Inside the housing is arranged a membrane 92, which covers a space connected with the inside of the reservoir, via said channels 30, and which is sealed around its periphery 920 to the surrounding inner wall of the housing. A foundation plate 93 with a bowl-shaped upper surface is arranged on the bottom plate 22. Holes 931 is arranged in the foundation plate 93 for connecting the space below the membrane 92 with the interior of the reservoir via said channels 30. A spring 94 is arranged in said space under the membrane. The spring is fastened between the foundation plate 93 and the membrane 92. The spring is arranged so that it is in unloaded state when the membrane is domed shaped as in FIG. 3.

An indicating button 95 is connected to the membrane 92 via a rod 921 which is fastened in the centre of the membrane and which has a cross section of such a small size that it only covers a minor part of the membrane. The indicating button comprises a bottom part 951 which has a colour that distinguish clearly from the housing 91. The indicating button has a top part 952 in a neutral colour and is provided with hooks 953 which are arranged to limit the buttons movement upwards through the opening 911 in the housing.

The leakage indicator is arranged to indicate when the pressure within the reservoir exceeds a predetermined pressure. The spring is arranged to cooperate with the pressure inside said space, i.e. the space below the membrane in the housing, against the atmospheric pressure such that said spring is arranged to be in compressed state when the pressure inside said space is at or below said predetermined pressure and that the spring is arranged to expand to bring the indicating button to become visible outside said surrounding wall of the housing 91 to indicate that the pressure inside the gas barrier exceeds said predetermined pressure.

An example of a suitable material in the membrane is a 80 μm thick film of PUR/EVOH/PUR where ethylene vinyl alcohol (EVOH) forms a gas barrier. Such a film is sold under the trade name Epurex LPT 9036. A suitable spring is spring No. 1128 from the company Lesjöfors Stockholms Fjäder AB.

Figure 4A:
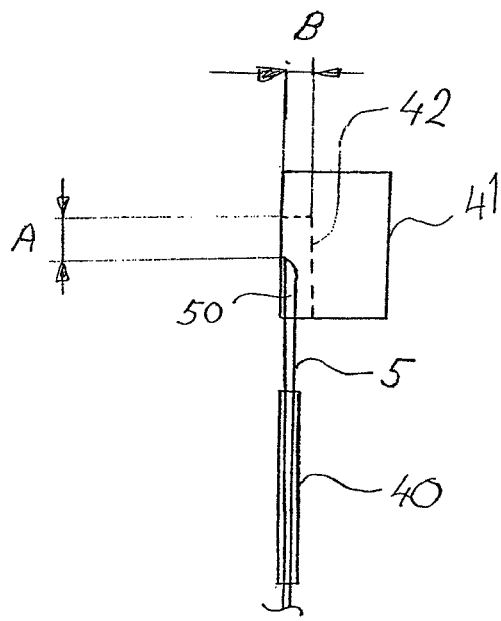
FIGS. 4a and 4b are schematic illustrations of a first example of the one-way valve at the inlet tube.
Figure 4B:
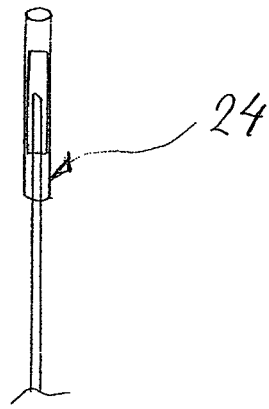

FIG. 4a shows how a first example of the one-way valve at the inlet tube can be manufactured. A tube 40 with a larger inner diameter than the outer diameter of the inlet tube is first treaded over the inlet tube. The outer diameter of the inlet tube is for instance about 2 mm. An advantage with such a thin tube compared with a thicker tube is that the tube can be sharply bent without any practical risk that the bending causes folds that block transportation of gas and liquid through the tube. A thin polyurethane film 41 coated with a silicone gel on one side is double folded over the end part 50 with gel against gel. The film 41 is suitably of a thickness of 20 μm and when applied of a size of 20×20 mm, i.e. a size that is manageable to handle. The folded film is adhered around the end part 50, with 10 mm on the tube 5 and 10 mm outside, and is cut along the broken line 42. The film is cut so that the folded film extends a distance A, suitably about 5 mm, outside the end of the tube and a distance B, of about 4 mm, sideways. The tube 40 is then treaded over the cut film so that the tube is arranged over the film as shown in FIG. 4b, i.e. extends about the same distance outside the both ends of the cut film. An example of a suitable silicone gel is a hydrophobic silicone gel marketed by Dow Corning under the trade name Dow-Corning Q7-22. A silicone gel layer of a thickness of approximately 40 g/m² applied on the film 41 works for the intended purpose. The formed one-way valve works as follows.

When a reduced pressure is generated by the suction pump the valve membrane formed by the part of the film which extends the distance A outside the end of the tube 5 forms an open channel which allows suction of air and liquid from the wound. If the pressure inside the reservoir increase above the pressure in the wound there is no risk that wound exudate is sucked back to the wound. The valve membrane or the channel formed by the film part which extends outside the end of the tube 5 will be pressed together and close the channel when the pressure outside the channel formed by the thin film is higher than the pressure in the channel. The silicone gel on the inside of the channel walls will adhere together and form a tight seal. The outer tube 40 works as a shield around the channel formed by said film part and the film part forming the membrane is only affected by the air pressure between the wound and the reservoir, i.e. any mechanical pressure around the one-way valve will be taken up by the outer tube 40. The one-way valve will open again when the pressure in the reservoir is reduced under the pressure within the wound. The one-way valve 24 described above is also illustrated in FIG. 2.

Figure 5A:
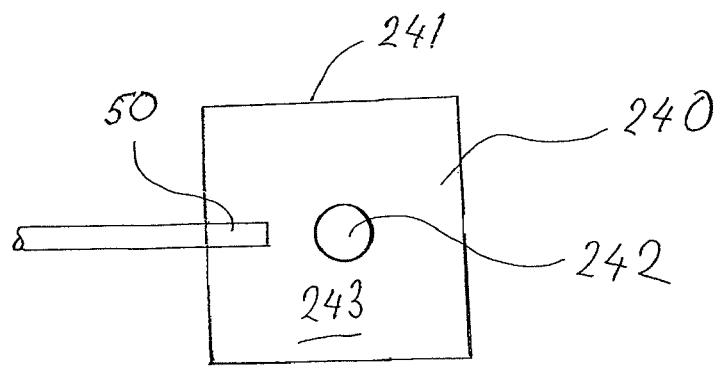
FIGS. 5a and 5b are schematic illustrations of a second example of the one-way valve at the inlet tube.
Figure 5B:
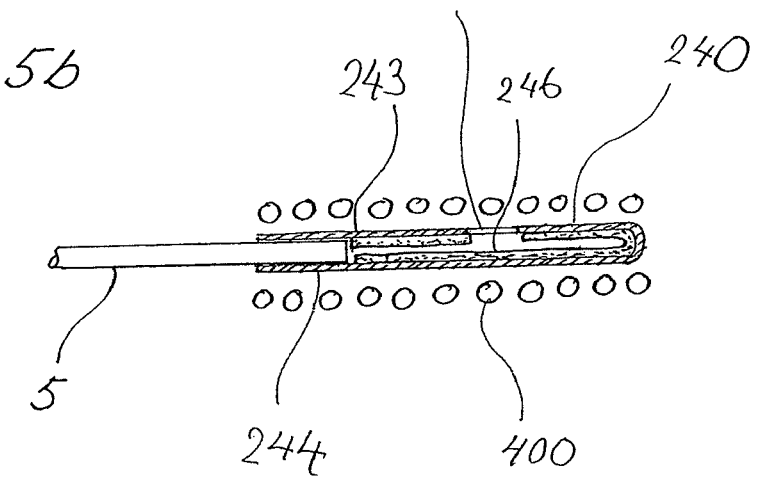

An alternative one-way valve is illustrated in FIGS. 5a and 5b.

The one-way valve 240 has the form of a bag with two main sides 243,244 and closed around its periphery 241 and sealed around the tube end for forming a bag inlet from the tube to the bag. The bag has an opening 242 on one 243 of said sides. The one-way valve is open with the two main sides at a distance from each other for allowing gas and liquid from the wound to pass into the bag via said bag inlet and out through said bag opening when the pressure around the bag is lower than at the wound. The one-way valve is closed with said main sides 243,244 pressed against each other around said bag opening when the pressure around the bag is higher than at the wound. The one-way valve 240 is shown in cross-section in FIG. 5b.

A shield 400, which fulfil the same purpose as the tube 40 in the embodiment according to FIGS. 4a and 4b, is schematically shown only in FIG. 5b, defines a space within which the bag can freely expand effected only by the pressure difference between the wound and the reservoir. The shield should be relatively form-stable and withstand mechanical pressure of sizes which can occur in the reservoir during use. The bag is preferably formed from a PUR-film with a thickness of about 20 μm and coated with a hydrophobic silicone gel layer of thickness of 40 g/m² on the sides which forms the inside of the bag. In FIG. 5b the silicone gel layer is designated with 246. As in the embodiment according to FIGS. 4a and 4b the silicone gel layer on the opposite main sides adheres against each other and forms a tight seal around the opening when the main sides 242 and 243 are pressed together.

Figure 6:
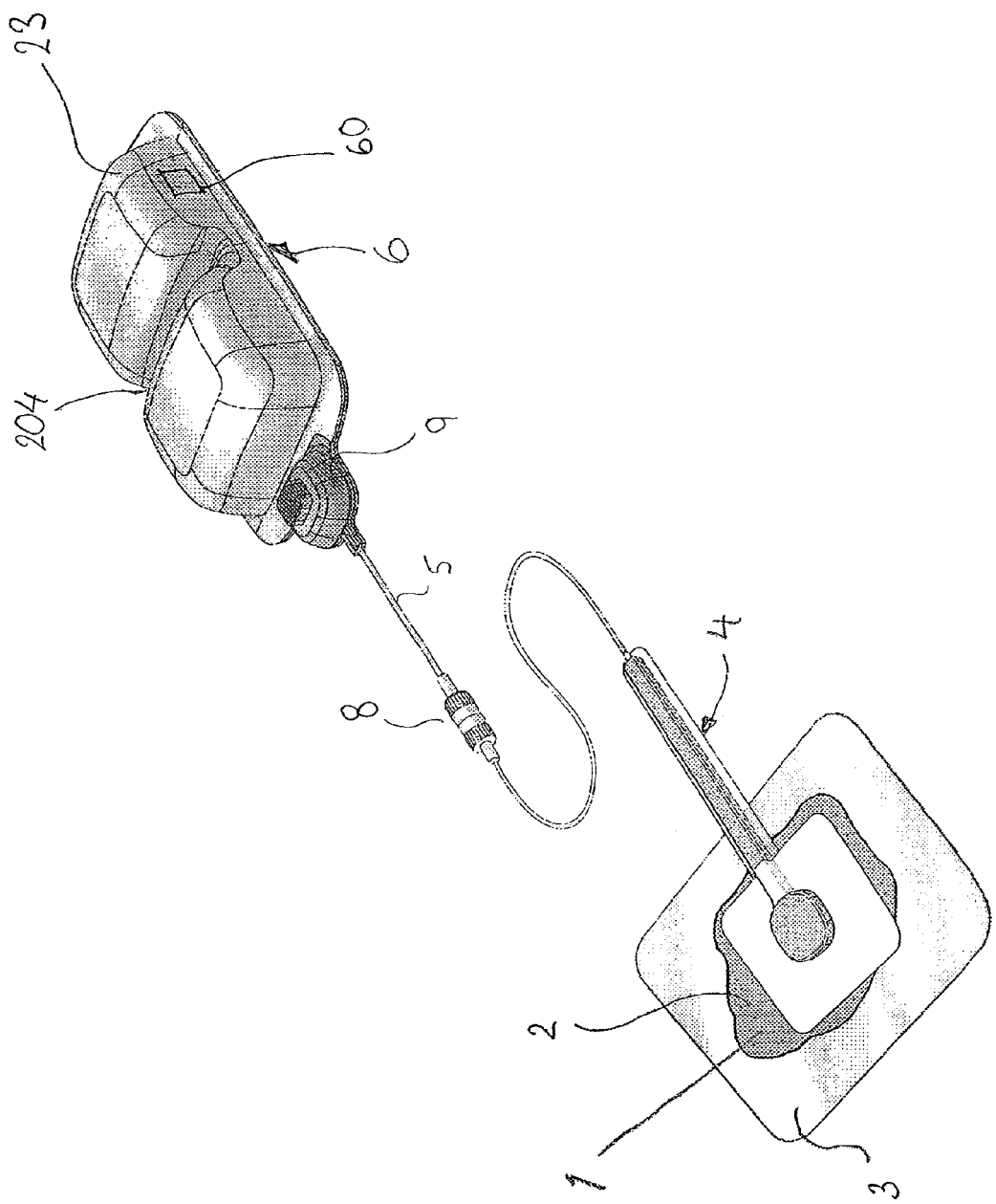
FIG. 6 shows schematically a second embodiment of the device in accordance with the invention.

In the embodiment according to FIG. 6 parts which corresponds to the same parts as in FIG. 1 has been provided with the same reference number. The reservoir 6 in the embodiment according to FIG. 6 lacks outlet tube and is not connected to an external pump. The remaining of the reservoir is formed as described in connection with FIG. 2 except for that a second one-way valve 60 is arranged in the cover, for instance in the plastic film 23 as indicated.

The first material 20 is, in the embodiment according to FIG. 6, arranged to serve as said suction unit and is capable of providing a reduced pressure upon manual compression. The second one-way valve 60 is arranged in the cover for allowing gas to flow out from said suction unit during compression but not in the opposite direction.

In a preferred embodiment the first material is an open-cell foam, that has a hinge 204 along which the foam can be bended and the second and third material and the cover are arranged to allow said bending. The hinge is arranged to mechanically divide the reservoir in two parts and the reservoir is foldable along said hinge for facilitate manual compression of the compressible first material.

The present invention is not limited to the embodiment described above, but a large number of modifications are possible within the scope of the patent claims below.

The invention claimed is:

1. A device for treatment of wounds using reduced pressure, said device comprising
    a pump capable of providing a reduced pressure,
    a gas barrier cover,
    a first compressible material adapted to elastically expand after compression,
wherein said first compressible material contains voids,
    a second material capable of absorbing wound fluids in an amount several times its own weight and retain the absorbed wound fluids,
wherein said first and second material are arranged inside the cover and form a reservoir connected to said pump,
said device further comprising
    an inlet for connecting the reservoir with a wound so as to allow the pump to expose the wound to the reduced pressure,
    a wound pad to be arranged in the wound cavity, and
    a sealing covering the wound and said wound pad,
wherein a third material is arranged around at least a major part of the first material, said third material having high liquid spreading capability, and that said second material is in the form of at least one layer arranged outside the third material and thereby separated from the first material by said third material.

2. A device in accordance with claim 1, wherein the inlet for wound fluids is arranged to run into the reservoir in connection to the third material.

3. A device in accordance with claim 1, wherein the first material has two opposite major outer surfaces, wherein said third material is arranged to enclose said major outer surfaces of said first material, and wherein layers of said second material are arranged outside said third material on both of said two opposite major outer surfaces of the first material.

4. A device in accordance with claim 1, wherein a one-way valve is arranged at the inlet inside the cover and allows gas and liquid to flow in the direction from the wound to the reservoir.

5. A device in accordance with claim 1, wherein said first material is an open-cell foam.

6. A device in accordance with claim 5, wherein a major part of said first material is enclosed in a breathable and liquid-tight layer, and wherein said layer is arranged between the first and the third material.

7. A device in accordance with claim 4, wherein said one-way valve is arranged in the end of a tube which in use of the device is connected with a wound, wherein said one-way valve is arranged to open for allowing gas and liquid from the wound to pass into the reservoir when said pump provides a reduced pressure, and wherein said one-way valve is closed when the pressure in the reservoir is higher than at the wound.

8. A device in accordance with claim 7, wherein said one-way valve comprises a thin, flexible PUR-film, which is arranged to form an open passage when said pump provides a reduced pressure, wherein said film is arranged to close said passage when the pressure in the reservoir is higher than at the wound, and wherein said one-way valve formed by the film is protected by a shield which is arranged to form a space within which said film is protected from other forces than caused by the pressure difference between the reservoir and the wound.

9. A device in accordance with claim 8, wherein said one-way valve has the form of a bag with two main sides and is closed around its periphery and sealed around said tube end for forming a bag inlet from the tube to the bag, that said one-way valve has a bag opening on at least one of said sides, wherein said one-way valve is open with the two main sides at a distance from each other for allowing gas and liquid from the wound to pass into the bag via said bag inlet and out through said bag opening when the pressure around the bag is lower than at the wound, wherein said one-way valve is closed with said main sides pressed against each other around said bag opening when the pressure around the bag is higher than at the wound, and wherein said shield defines a space within which the bag can freely expand affected only by the pressure difference between the wound and the reservoir.

10. A device in accordance with claim 9, wherein said bag opening is arranged to lead directly to the third material.

11. A device in accordance with claim 8, wherein said one-way valve is formed by a mainly rectangular thin film applied around said tube end and forming a tubular passage which extends partly over an end part at said tube end and extends further outside said tube end for forming a flexible outer valve part, wherein the film forming the passage is arranged to be pressed together for closing the passage when the pressure in the reservoir exceeds the pressure in the wound and is arranged to open the passage when a reduced pressure is applied in the reservoir, and wherein the shield is in form of a protecting tube applied at least over the length of said tubular passage, which protecting tube has an inner diameter which is larger than the outer diameter of said tubular passage.

12. A device in accordance with claim 1, wherein said first material is arranged to serve as said pump and is capable of providing a reduced pressure upon manual compression, and wherein a second one-way valve is arranged in said cover for allowing gas to flow out from said pump during compression.

13. A device in accordance with claim 1, wherein said first material is an open-cell foam, wherein said first material has at least one hinge along which the foam can be bended, and wherein the second and third material and the cover are arranged to allow said bending.

14. A device in accordance with claim 13, wherein said hinge is arranged to mechanically divide the reservoir in two parts, and wherein the reservoir is foldable along said hinge to facilitate manual compression of the compressible first material.

15. A device in claim 1, wherein said pump is electrical with a capacity of providing a reduced pressure of at least 10 kPa.

* * * * *

UNITED STATES PATENT AND TRADEMARK OFFICE
CERTIFICATE OF CORRECTION

PATENT NO. : 8,382,731 B2  Page 1 of 1
APPLICATION NO. : 12/936756
DATED : February 26, 2013
INVENTOR(S) : Ulf Johannison It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 182 days.

Signed and Sealed this
First Day of September, 2015

Michelle K. Lee
*Director of the United States Patent and Trademark Office*